United States Patent [19]

Seferian et al.

[11] 3,976,467
[45] Aug. 24, 1976

[54] UREA GYPSUM ADDITION PRODUCT AND METHOD

[76] Inventors: Rupen B. Seferian, 1372 N. Grand Oaks, Pasadena, Calif. 91109; Roy M. Kaprielian, 1140 Oakwood Drive, San Marino, Calif. 91108

[22] Filed: Aug. 25, 1975

[21] Appl. No.: 607,150

[52] U.S. Cl. .................................. 71/28; 71/63; 106/109; 260/553 R; 260/555 S
[51] Int. Cl.² ................... C05C 9/00; C04B 11/00; C07C 126/00; C07C 127/00
[58] Field of Search ............ 71/1, 28, 63; 106/109, 106/110, 111, 306, 308 N; 260/553 CD, 553 R, 555 S, 555 C

[56] References Cited
UNITED STATES PATENTS
2,157,541   5/1939   Hosokawa............................ 71/28

Primary Examiner—Charles N. Hart
Assistant Examiner—Lander Ferris H.
Attorney, Agent, or Firm—Louis J. Bachand

[57] ABSTRACT

Soil supplement and plant nutrient and method therefor the supplement nutrient having the empirical formula $$(CaSO_4)_2 \cdot 2CO(NH_2)_2$$

and being prepared by replacing the normal two waters of hydration of gypsum with urea by controlled heating in the substantial absence of unbound water. The product is a persistent nutrient.

10 Claims, No Drawings

UREA GYPSUM ADDITION PRODUCT AND METHOD

BACKGROUND OF THE INVENTION

This invention has to do with soil nutrition and supplementation and more particularly with a conventional soil supplement-dihydrate gypsum-converted to be a plant nutrient as well through the addition of urea to the gypsum, in bimolecular substitution, rather than higher levels of urea in addition products with gypsum, for increased persistence of effect.

The invention is most particularly concerned with method enabling addition of two moles of urea onto two calcium sulfate moieties from gypsum.

PRIOR ART

Others have treated gypsum with urea, under different conditions than herein and with different results. For example Whittaker in U.S. Pat. No. 2,074,880 teaches the obtaining of a product he donominates as $CaSO_4 \cdot 4CO(NH_2)_2$, note four moles of urea, and by a reaction scheme involving inter alia preparation of a more than saturated solution of urea in water, to which is added a quality of gypsum, or alternatively, mixing of finely ground urea and gypsum, to have typical ratios of three to four moles of urea to one mole of gypsum. See also U.S. Pat. No. 2,157,541 to Hosokawa for a teaching of a preparation of a similar product. U.S. Pat. No. 1,977,628 to Hall is another patent teaching higher ratios of urea to gypsum than in the present method, indeed reverse ratios. Other patents considered in the preparation of the application being all the patents developed in a search of the prior art include: U.S. Pat. No. 1,889,960 to Hintzmann; U.S. Pat. No. 2,801,911 to Gilbert et al; U.S. Pat. No. 2,991,221 to Bryant et al; U.S. Pat. No. 3,684,476 to Wadsted; and U.S. Pat. No. 3,785,796 to Mann, Jr.

SUMMARY OF THE INVENTION

In a departure from the teachings of the prior art and for purposes of readily preparing in a facile manner a directly usable soil supplement and plant nutrient having advantageously a higher ratio of gypsum to urea than heretofore available in the above-mentioned prior art, the invention provides method for the conversion of dihydrate gypsum soil supplement into plant nutrient containing nutriently effective levels of slowly soil releasable urea, which method includes controllably displacing the two waters of hydration of the gypsum with only two moles of urea to form an addition product having the empirical formula $$(CaSO_4)_2 \cdot 2CO(NH_2)_2$$

by the steps of slowly driving the two waters of hydration from the gypsum in an intimate reaction mixture substantially free of unbound water and comprising the gypsum and urea in a molar ratio of three to four moles of gypsum per mole of urea, at a temperature between 95° and 140°C, to form the addition product within the reaction mixture, and cooling the reaction mixture to a frangible solid comprising the addition product.

In particular embodiments, the method also includes intimately interdispersing the gypsum and urea at room temperature to form the reaction mixture and thereafter heating to the mentioned reaction temperature; absorbing or binding free water into the urea in an amount less then dissolves the urea granules in advance of the interspersing of the urea with the gypsum; preheating the urea reagent in advance of interdispersing with the gypsum reagent; heating the urea reagent to a temperature above about 110°C, and thereafter adding the gypsum reagent thereto.

Additionally the invention contemplates employment of a molar ratio of reagents in the reaction mixture of three moles of gypsum per mole of urea and also absorbing up to 8% by weight free water into the urea, heating the urea to a temperature above about 110°C, and thereafter adding the gypsum thereto.

There is formed by the foregoing method an addition product having but two moles of urea and the empirical formula:

$$(CaSO_4)_2 \cdot 2CO(NH_2)_2$$

DESCRIPTION OF THE PREFERRED EMBODIMENTS

In carrying out the invention use is made of gypsum, a naturally occurring mineral having usually the formula $CaSo_4 \cdot 2H_2O$ and it is this dihydrate from to which reference is made in the specification and claims. It is known to employ gypsum as a soil supplement and modifier, for example, in the soil used for leguminous crops and peanuts. It appears that finely ground gypsum, mixed with manure, for example, acts to stabilize volatile, dissolved nitrogenous compounds thus preventing their loss by volatilization and leaching. See Section: Calcium Compounds, Kirk-Othmer Encyclopedia. As such, however, gypsum is not considered a fertilizer or plant nutrient. Accordingly, there is need to so modify or treat gypsum that the addition of the treated gypsum to the soil will effect plant nutrition as well as supplement the soil.

For this purpose, the present process employs urea, a known plant nutrient having the formula $CO(NH_2)_2$, but in a highly effective form: a dimolecular addition product with gypsum. In this form the urea, which is of course a plant nutrient, is held readily but slowly available in the soil through slow, timed release from the addition compound or complex.

The effectiveness of the combination of gypsum and only two moles of urea in accordance with the invention, rather than three or four as has been previously known appears to lie in the acid-base balance realized with the instant molar ratio. Thus, while not wishing to be found to any particular theory of operation, it is believed that gypsum, a soil acidifier, normally acts to neutralize the soil, while urea is basic in nature. The presence of two mole of urea, held to the gypsum by acid-base balance bonding, electronegatively or coordinate or possibly hydrogen bonding, places an effective near neutralizing amount of urea in proximity to the acid radical of the gypsum, avoiding over-basicity which may result from the presence of three to four moles of urea.

The invention will be further described as to an illustrative embodiment in the following examples in which all parts and percentages are by weight.

EXAMPLE 1

Commercial grade urea initially containing about one percent (1%) water was heated to about a melt condition by gypsum was added slowly thereto to proportions of four moles of gypsum per mole of urea, with stirring, and dropping the temperature to about 110°C, the mixture was allowed to cool, in the air on a screen. The product mass of friable granules are analyzed to the formula $(CaSO_4)_2 \cdot (NH_2)_2$.

EXAMPLE 2

The procedure of Example 1 was modified to intimately admix gypsum and urea in the proportion of Example 1, the urea again initially containing between one percent (1%) and five percent (5%) water absorptively bound thereto. The mixture was heated to between 95° and 140°C, reacted to an addition product of the formula of Example 1 and allowed to cool to a frangible mass.

EXAMPLE 3

Example 1 is a duplicated but first moistening the granular urea to contain five percent (5%) water, an amount insufficient to dissolve the granules, heating the urea to 110°C and adding between three and four moles of gypsum thereto, per mole of urea.

EXAMPLE 4

Example 1 is duplicated using four moles of gypsum per mole of urea. Results are equivalent.

EXAMPLE 5

The composition of Examples 1 to 4 together with a like weight of urea (Control I) and a like weight of gypsum (Control II) are evaluated as soil supplement and plant nutrient in a garden in which limas, zucchini and tomatoes are to be grown. The compositions are added to the soil in adjacent rows with the Control I and Control II additions being on opposite sides of the Example 1 to 4 rows.

The mentioned vegetables, grown from seedlings over a season in each of the Examples 1 to 4 rows are larger, bear heavier fruit and are more drought tolerant than the like seedlings plants in the outside, Control I and II rows.

EXAMPLE 6

Persistence of the product is demonstrated by the continued nutrition of grape vines, via urea nitrogen release, reflected in heavier crop production, even after three years have passed from the initial and sole application of the material.

CONTROL III

An addition product of gypsum with four moles of urea is evaluated as a plant nutrient at levels of application comparable to those in Example 5 from a fruit product standpoint the soil appeared exhausted of nutrient in less than one growing season.

We claim:

1. Method for conversion of dihydrate gypsum soil supplement into a plant nutrient containing slowly soil-releasable urea by controllably displacing the two waters of hydration of the gypsum with only two moles of urea to form an addition product having the empirical formula $$(CaSO_4)_2 \cdot 2CO(NH_2)_2$$

the method including slowly driving the two waters of hydration from the gypsum in an intimate reaction mixture substantially free of unbound water and comprising said gypsum and urea in a molecular ratio of three to four moles of gypsum per mole of urea, at a temperature between about 95° and 140°C to form said addition product within the reaction mixture, and cooling the reaction mixture to a frangible solid comprising said addition product.

2. Method according to claim 1 including also intimately interdispersing said gypsum and urea at room temperature to form said reaction mixture and thereafter heating to said temperature.

3. Method according to claim 2 in which said urea reagent is granular and including also absorbing free water into said urea in an amount less than dissolves said urea granules in advance of interdispersing the urea with gypsum.

4. Method according to claim 3 including also preheating said urea reagent in advance of interdispersing with the gypsum reagent.

5. Method according to claim 4 including also heating the urea reagent to a temperature above about 110°C and thereafter adding said gypsum reagent thereto.

6. The product formed by the method of claim 5.

7. Method according to claim 1 in which the molar ratio of reagent in the reaction mixture is three moles of gypsum per mole of urea.

8. Method according to claim 7 including also absorbing up to 8% by weight free water into said urea, heating the urea to a temperature above about 110°C and thereafter adding said gypsum thereto.

9. The product formed by the method of claim 7.

10. $(CaSO_4)_2 \cdot 2(CONH_2)_2$.

* * * * *